United States Patent [19]
Morris

[11] Patent Number: 5,951,509
[45] Date of Patent: Sep. 14, 1999

[54] BLOOD PRODUCT IRRADIATION DEVICE INCORPORATING AGITATION

[75] Inventor: Livingston B. Morris, Devon, Pa.

[73] Assignee: Therakos, Inc., Exton, Pa.

[21] Appl. No.: 08/971,879

[22] Filed: Nov. 19, 1997

Related U.S. Application Data

[60] Provisional application No. 60/031,907, Nov. 27, 1996, and provisional application No. 60/046,794, Apr. 18, 1997.

[51] Int. Cl.⁶ .................................................. A61M 37/00
[52] U.S. Cl. .......................... 604/4; 604/5; 604/6; 435/2; 422/24; 250/432 R; 250/455.11
[58] Field of Search ..................... 604/4, 5, 6, 7; 422/22, 24, 44; 435/2; 250/432 R, 433, 453.11, 454.11, 455.11, 492.1

[56] References Cited

U.S. PATENT DOCUMENTS

| | | |
|---|---|---|
| 4,321,919 | 3/1982 | Edelson . |
| 4,398,906 | 8/1983 | Edelson . |
| 4,428,744 | 1/1984 | Edelson . |
| 4,464,166 | 8/1984 | Edelson . |
| 4,568,328 | 2/1986 | King . |
| 4,573,960 | 3/1986 | Goss . |
| 4,573,961 | 3/1986 | King . |
| 4,578,056 | 3/1986 | King et al. . |
| 4,596,547 | 6/1986 | Troutner . |
| 4,608,255 | 8/1986 | Kahn et al. ............................. 424/101 |
| 4,617,279 | 10/1986 | Manabe et al. . |
| 4,623,328 | 11/1986 | Hartranft . |
| 4,643,710 | 2/1987 | Troutner . |
| 4,647,279 | 3/1987 | Mulzet et al. . |
| 4,681,568 | 7/1987 | Troutner . |
| 4,692,138 | 9/1987 | Troutner et al. ............................ 604/4 |
| 4,705,498 | 11/1987 | Goss . |
| 4,708,712 | 11/1987 | Mulzet . |
| 4,708,715 | 11/1987 | Troutner et al. . |
| 4,726,949 | 2/1988 | Miripol et al. . |
| 4,727,027 | 2/1988 | Wiesehahn et al. . |
| 4,737,140 | 4/1988 | Lee et al. . |
| 4,850,995 | 7/1989 | Tie et al. . |
| 4,866,282 | 9/1989 | Miripol et al. ....................... 250/455.1 |
| 4,952,812 | 8/1990 | Miripol et al. . |
| 5,010,968 | 4/1991 | Barrow .................................... 177/118 |
| 5,133,932 | 7/1992 | Gunn et al. ............................... 422/24 |
| 5,147,330 | 9/1992 | Kogel ...................................... 604/245 |
| 5,150,705 | 9/1992 | Stinson ........................................ 604/4 |
| 5,433,738 | 7/1995 | Stinson .................................... 607/92 |
| 5,459,322 | 10/1995 | Warkentin . |
| 5,482,828 | 1/1996 | Lin et al. . |
| 5,792,867 | 6/1998 | D'Silva .................................... 422/44 |
| 5,846,437 | 12/1998 | Whitby et al. .......................... 210/248 |
| 5,868,695 | 2/1999 | Wolf, Jr. et al. ............................ 604/4 |
| 5,871,459 | 2/1999 | Muller ........................................ 604/4 |
| 5,871,702 | 2/1999 | Kutner et al. ........................... 422/299 |
| 5,872,365 | 2/1999 | Goh et al. ............................. 250/492.1 |

FOREIGN PATENT DOCUMENTS

| | | | |
|---|---|---|---|
| 0030358 | 11/1979 | European Pat. Off. ................... 604/6 |
| 2100143 | 11/1982 | United Kingdom ....................... 604/6 |

OTHER PUBLICATIONS

International Search Report Application No. PCT/US97/21490 dated Nov. 19, 1997.

Extracorporeal Photochemotheraphy: Evaluation of Two Techniques and Use in Connective Tissue Disorders vol. 15, No. 4 Dec. 1994, Transfusion Science pp. 443–454.

*Primary Examiner*—John G. Weiss
*Assistant Examiner*—Joseph F. Weiss, Jr.

[57] ABSTRACT

Apparatus for treating human blood by irradiation. Exposure of a human blood product sample can be optimized by displacing a contiguous, self-contained arrangement, such as a bag member, while radiation is being emitted towards the contiguous, self-contained arrangement, and by maintaining a substantially constant distance between the radiation source and the at least one blood product held in the contiguous, self-contained arrangement. Also proposed is an arrangement in which at least a portion of the radiation source is displaced while radiation is being emitted towards the contiguous, self-contained arrangements holding the blood products in question. Further, an arrangement for cooling the radiation source is contemplated.

18 Claims, 9 Drawing Sheets

BLOOD PRODUCT IRRADIATION DEVICE INCORPORATING AGITATION

This application claims priority to Provisional U.S. application No. 60/031,907, filed Nov. 27, 1996, and Provisional U.S. application No. 60/046,794, filed Apr. 18, 1997.

FIELD OF THE INVENTION

The present invention generally relates to methods and apparatus for treating human blood and/or blood products. More particularly, the present invention relates to methods and apparatus for irradiating, e.g. with ultraviolet light, human blood and/or blood products.

BACKGROUND OF THE INVENTION

It is well-known that a number of human disease states may be characterized by the over-production of certain types of leukocytes, including lymphocytes, in comparison to other populations of cells that normally comprise whole blood. Excessive or abnormal lymphocyte populations can result in numerous adverse effects to patients, including the functional impairment of bodily organs, leukocyte-mediated autoimmune diseases and leukemia-related disorders.

As a result, there have been proposed numerous apparatus and processes for treating human blood in such a manner as to moderate the viability of given cellular populations in order to provide relief for patients suffering from diseases and disorders such as those discussed above. Generally, such apparatus and processes involve the treatment of blood with a drug that is capable of forming photoadducts with DNA in the presence of certain types of radiation, such as ultraviolet (or "U.V.") radiation.

The bulk of such conventionally known apparatus and processes involve what is termed "extracorporeal" irradiation, whereby the irradiation of the blood or blood products takes place away from the body of the patient. Some conventional apparatus and processes involving extracorporeal irradiation are to be found in the following U.S. patents to R. Edelson: U.S. Pat. Nos. 4,321,919; 4,398,906; 4,428,744; and 4,464,166. Also, the article "Treatment of Leukemia. CTCL with extracorporeally photoactivated 8-MOP" by R. Edelson et al. (American Association of Clinical Investigators, Annual Meeting, May 1, 1983, Washington, D.C.) provides further background information on this subject.

Departing from known apparatus and processes such as those alluded to above, various refinements have been made with the objective of increasing the efficiency, safety and accuracy of the irradiation procedures being performed.

For example, U.S. Pat. No. 4,727,027 to Wieshahn et al. discloses the decontamination of blood and blood components via treatment with furocoumarin derivatives, followed by irradiation, with UV-A radiation having a wavelength between about 300–400 nm, at an intensity between 0.1 mW/cm and 5.0 w/cm.

U.S. Pat. No. 5,459,322 to Warkentin discloses methods and apparatus for exposing a blood-based sample to ultraviolet radiation. Particularly, a sample contained within a shielded housing is permitted to be exposed to a source of ultraviolet radiation and simultaneously observed. The sample rests on a stage that can be moved relative to the source of the ultraviolet radiation while the irradiation is taking place, so that the effect of ultraviolet radiation upon given biological materials (such as blood) can be determined. It is contemplated therein that the movement of the stage be controlled by a set of lead screws.

The article "Extracorporeal Photochemotherapy: Evaluation of Two Techniques and Use in Connective Tissue Disorders", by G. Andreu et al., as found in *Transfusion Science*, Vol. 15, No. 4, pp. 443–454 (1994), compares and contrasts two different techniques for irradiating human blood.

There are disclosed, in U.S. Pat. Nos. 4,850,995, 4,708,712, and 4,647,279 (to Tie et al.; Mulzet; and Mulzet et al., respectively), some methods and apparatus involving the centrifugal separation of blood.

Finally, it is known to use, for irradiation during photophoresis procedures, an arrangement that includes a recirculating pump chamber, a conventional intravenous ("I.V.") bag, and an irradiation chamber, as well as tubing for interconnecting the bag with the irradiation chamber. In one such known device, the bag is designed to create a vortex therewithin, in order to keep the blood products evenly mixed. Also, a separate roller pump is used for the purpose of recirculating the blood products. At least portions of this known device, and components therefor, are contemplated in several U.S. patents, including: U.S. Pat. No. 4,708,715 to Troutner et al.; U.S. Pat. No. 4,692,138 to Troutner et al. and U.S. Pat. No. 4,737,140 to Lee et al.

As a matter of further explanation, a device such as that described immediately above often involves what may be termed a "closed-loop" system of circulating blood products through an irradiation chamber. In this respect, an irradiation chamber is provided with essentially rigid through-passages, whereby a bag (or what may be alternatively termed a "vortex bag") feeds into the through-passages of the irradiation chamber via the aforementioned interconnecting tubing. Likewise, portions of the aforementioned interconnecting tubing feed irradiated blood products back to the "vortex bag." Upon the achievement of a predetermined number of flow cycles, i.e., from the "vortex bag" to the irradiation chamber and back, the "vortex bag" is removed and subsequently mounted in a manner that permits propagation of the irradiated blood products back to the patient.

U.S. Pat. Nos. 4,952,812, and 4,726,949, both to Miropol et al., disclose methods in which a thin film of white blood cells are irradiated within the UV-B band at a wavelength of 280–320 nanometers (nm). These two patents to Miropol et al. also appear to disclose arrangements for accommodating a flat, flexible bag in an ultraviolet irradiation apparatus, and contemplate that, for the irradiation process, blood cells be provided in a thin film that is inserted between two banks of UV-B bulbs mounted a fixed distance apart, within a specially designed cabinet.

Generally, the apparatus and processes proposed to date, including those disclosed in the patents and publications discussed hereinabove, have often involved the use of arrangements, components, and procedures that can tend to be complex and expensive. Further, many of the apparatus and processes proposed to date, including many of those disclosed in the patents and publications discussed hereinabove, have often failed to: adequately irradiate blood products continuously with U.V. light; prevent stagnation of the blood products and evenly expose all constituents; adequately control the temperature of the blood products being irradiated; adequately afford access to irradiation lamps; be appropriately sized so as to facilitate incorporation into a greater apparatus or instrument; and adequately protect users from harmful U.V. light and aerosols.

Accordingly, an advantage would appear to exist in connection with:

an arrangement for irradiating blood products continuously and effectively with U.V. light while providing gentle agitation to prevent stagnation and to evenly expose all constituents;

adequate control of the temperature of blood products being irradiated;

easy access to irradiation lamps to facilitate their renewal or replacement; and protection of the user from harmful U.V. light and aerosols.

SUMMARY OF THE INVENTION

In an apparatus and/or process contemplated by at least one preferred embodiment of the present invention, an irradiation bag is placed on a horizontal platen which has a lamp array attached to the underside of the platen. An upper glass platen and lamp array is hinged to the lower platen in such a manner that sufficient space is maintained between the platens to accommodate the bag while the assembly is rocked through a small displacement by a small motor bearing a roller cam upon which the lower platen rests. The lower platen, in turn, can be hinged to a base plate, so that the entire assembly can be unfolded to expose the lamp arrays for easy changing of the individual bulbs.

The entire assembly can preferably be housed in a close-fitting shroud with a hinged top. The shroud, as such, can serve to duct air past the bag and lamps in order to control the temperature of the ultraviolet lighting (i.e., "the U.V. flood"), and also to contain the ultraviolet light (i.e., for the safety of the operator). Air can be drawn by a blower through the shroud into a plenum having a filter on the outlet side of the blower, with the filler serving to trap any aerosols that could be created by a leak in any of a number of portions of the assembly.

In summary, one aspect of the present invention broadly contemplates apparatus for treating human blood, the apparatus including:

a radiation-permeable arrangement for holding at least one human blood product;

an arrangement for irradiating at least one human blood product held in the radiation-permeable holding arrangement; and an arrangement for displacing at least a portion of the irradiating arrangement at least during irradiation of the at least one blood product.

In another aspect, the present invention broadly contemplates apparatus for treating human blood, the apparatus including:

an arrangement for withdrawing blood from a human patient;

an arrangement for separating blood, having been withdrawn from a human patient by the withdrawing arrangement, into selected blood products;

an arrangement for temporarily storing at least one blood product having been separated by the separating arrangement;

the storing arrangement comprising a contiguous, self-contained arrangement, the contiguous, self-contained arrangement comprising a port arrangement for permitting the entry and egress of at least one blood product into and out of the contiguous, self-contained arrangement;

an arrangement for irradiating at least one blood product held in the contiguous, self-contained arrangement, the irradiating arrangement comprising a radiation source for emitting radiation towards the contiguous, self-contained arrangement;

an arrangement for supporting the contiguous, self-contained arrangement while radiation is being emitted towards the contiguous, self-contained arrangement from the radiation source;

an arrangement for optimizing exposure of at least one blood product being held in the contiguous, self-contained arrangement to radiation emitted by the radiation source while radiation is being emitted towards the contiguous, self-contained arrangement from the radiation source; and the arrangement for optimizing exposure comprising:

an arrangement for displacing the contiguous, self-contained arrangement while radiation is being emitted towards the contiguous, self-contained arrangement from the radiation source, to displace the at least one blood product held within the contiguous, self-contained arrangement and maximally expose the at least one blood product to the radiation emitted by the radiation source; and an arrangement for maintaining a substantially constant distance between the radiation source and the at least one blood product held in the contiguous, self-contained arrangement during displacement of the contiguous, self-contained arrangement.

In yet another aspect, the present invention broadly contemplates apparatus for irradiating blood products having been withdrawn from a human patient and having been separated in an arrangement for separating blood into selected blood products, the apparatus including:

an arrangement for temporarily storing at least one blood product;

the storing arrangement comprising a contiguous, self-contained arrangement, the contiguous, self-contained arrangement comprising a port arrangement for permitting the entry and egress of at least one blood product into and out of the contiguous, self-contained arrangement;

an arrangement for irradiating at least one blood product held in the contiguous, self-contained arrangement, the irradiating arrangement comprising a radiation source for emitting radiation towards the contiguous, self-contained arrangement;

an arrangement for supporting the contiguous, self-contained arrangement while radiation is being emitted towards the contiguous, self-contained arrangement from the radiation source;

an arrangement for optimizing exposure of at least one blood product being held in the contiguous, self-contained arrangement to radiation emitted by the radiation source while radiation is being emitted towards the contiguous, self-contained arrangement from the radiation source; and the arrangement for optimizing exposure comprising:

an arrangement for displacing the contiguous, self-contained arrangement while radiation is being emitted towards the contiguous, self-contained arrangement from the radiation source, to displace the at least one blood product held within the contiguous, self-contained arrangement and maximally expose the at least one blood product to the radiation emitted by the radiation source; and an arrangement for maintaining a substantially constant distance between the radiation source and the at least one blood product held in the contiguous, self-contained arrangement during displacement of the contiguous, self-contained arrangement.

Still another aspect of the present invention broadly contemplates apparatus for irradiating blood products having been withdrawn from a human patient and having been separated in an arrangement for separating blood into selected blood products, the apparatus including:

an arrangement for temporarily storing at least one blood product;

the storing arrangement comprising a contiguous, self-contained arrangement, the contiguous, self-contained arrangement comprising a port arrangement for permitting the entry and egress of at least one blood product into and out of the contiguous, self-contained arrangement;

an arrangement for irradiating at least one blood product held in the contiguous, self-contained arrangement, the irradiating arrangement comprising a radiation source for emitting radiation towards the contiguous, self-contained arrangement;

a housing arrangement for encasing the irradiating arrangement;

an arrangement for supporting the contiguous, self-contained arrangement while radiation is being emitted towards the contiguous, self-contained arrangement from the radiation source;

an arrangement for optimizing exposure of at least one blood product being held in the contiguous, self-contained arrangement to radiation emitted by the radiation source while radiation is being emitted towards the contiguous, self-contained arrangement from the radiation source; and an arrangement for cooling the radiation source while radiation is being emitted toward the contiguous, self-contained arrangement from the radiation source.

Still yet another aspect of the present invention broadly contemplates apparatus for irradiating at least one blood product, such at least one blood product originating from an arrangement for separating, into selected blood products, blood that has been withdrawn from a human patient, and has been transferred into a contiguous, self-contained arrangement being permeable to radiation emitted from the apparatus; the apparatus including:

a radiation source for emitting radiation towards a contiguous, self-contained arrangement, to irradiate at least one blood product held within the contiguous, self-contained arrangement;

an arrangement for supporting the contiguous, self-contained arrangement during irradiation of at least one blood product held within the contiguous, self-contained arrangement;

an arrangement for optimizing exposure of at least one blood product held in the contiguous self-contained arrangement to radiation emitted by the radiation source while the at least one blood product is being irradiated; and the arrangement for optimizing exposure comprising arrangement for displacing at least a portion of the radiation source while radiation is being emitted towards the contiguous, self-contained arrangement from the radiation source.

BRIEF DESCRIPTION OF THE DRAWINGS

The present invention will become more readily apparent from the following description of preferred embodiments therefor shown, by way of example only, in the accompanying drawings, wherein.

DESCRIPTION OF THE PREFERRED EMBODIMENTS

Figure 1:
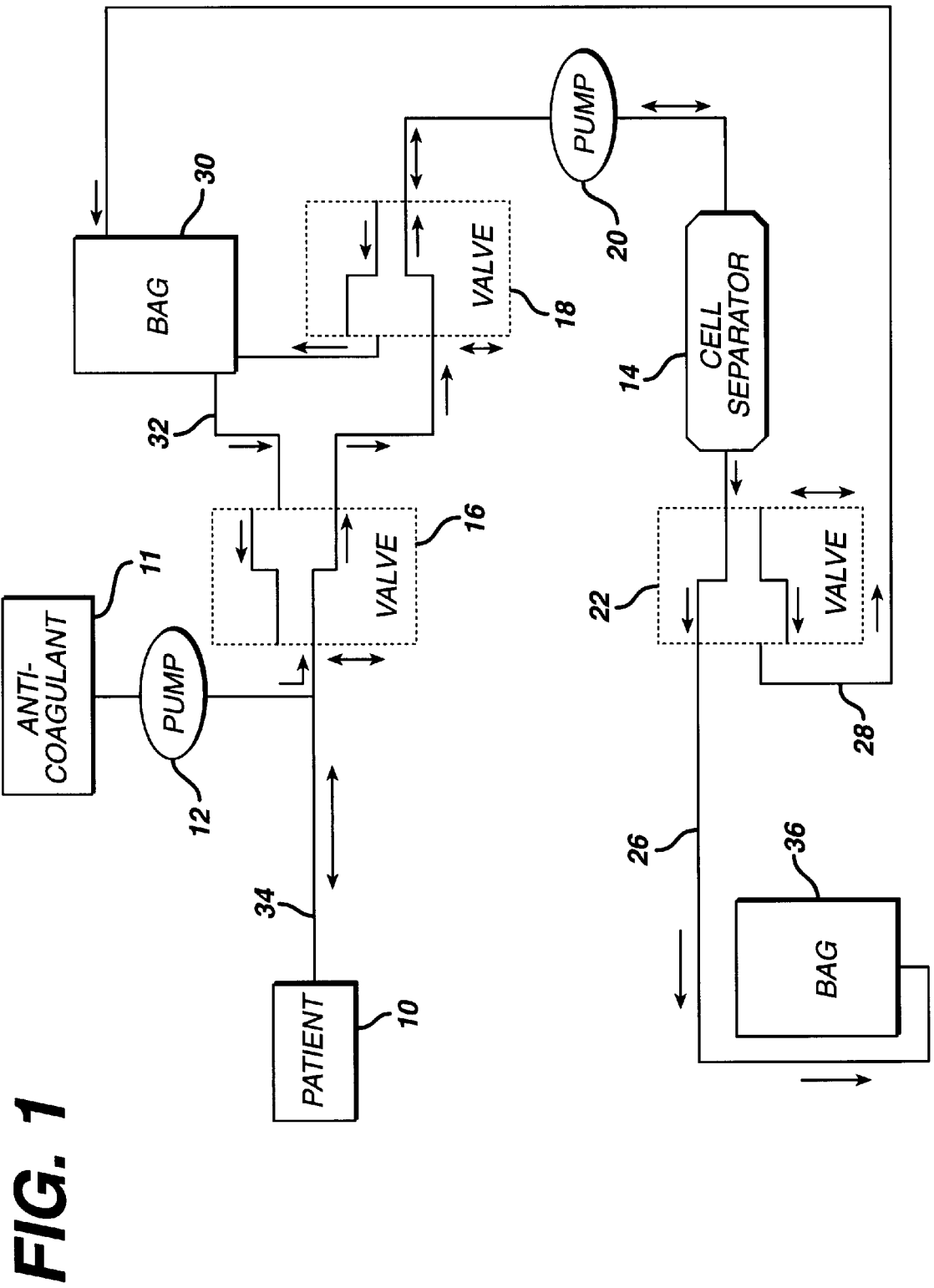
FIG. 1 is a schematic illustration of a blood product irradiation device.

FIG. 1 is a schematic illustration of the general arrangement of the fluid handling components a blood product irradiation device according to a preferred embodiment of the present invention. It is to be understood that the general arrangement schematically illustrated in FIG. 1 is provided for illustrative purposes and broadly contemplates the use of any of several suitable components and devices. Specific examples of such components and devices will be discussed throughout the instant specification and, where indicated, may also be disclosed in any of several U.S. patents that are variously cited throughout the instant specification.

Generally, in accordance with known processes and devices relating to blood product irradiation, it may be assumed that a patient, generally indicated at 10, will have his or her blood withdrawn via a suitable blood withdrawal line or conduit 34.

Upon the blood being withdrawn from the patient 10, it may be appropriate to add an anti-coagulant solution to the blood, possibly with the assistance of a pump 12. Such anti-coagulants will be generally well-known to those of ordinary skill in the art, and will thus not be discussed in further detail herein.

Essentially, the patient's blood will be destined for separation in a cell separator 14, such as a centrifuge, or other suitable blood separation device. Generally, the purpose of directing the blood to cell separator 14 will be to separate the blood into two or more portions, whereby only a given portion or portions of the blood will actually be destined for irradiation. The remainder of the blood, which may be termed the "nonirradiated" blood products, will preferably be destined for a suitable plastic or polyurethane bag in order that the "nonirradiated" blood products may either be held in storage or returned to the patient.

Continuing, the patient's blood, possibly after being supplemented by an anti-coagulant (as described heretofore), will preferably pass through a suitable valve arrangement 16, the function and significance of which will be more readily appreciated further below. The patient's blood may thence preferably proceed to yet another valve arrangement 18, the function of which will also be more readily appreciated further below. Consequently, and possibly with the assistance of a pump 20, the patient's blood will proceed to cell separator or centrifuge 14.

Thence, the patient's blood will preferably be run through the centrifuge 14, and subsequently separated as described herebelow:

In accordance with any of several well-established conventional procedures, a first portion of the patient's blood, conceivably a portion containing a preponderance of white blood cells, will, upon separation, be removed from the cell separator or centrifuge 14. This first portion will preferably correspond to blood products that are destined for irradiation. Subsequently, a second portion of the patient's blood, conceivably exhibiting a paucity of white blood cells, will, upon separation be similarly be removed from the centrifuge.

Generally, upon exiting the cell separator or centrifuge 14, a selected component or components of the patient's blood, that is, a predetermined blood product or products, will preferably proceed to a valve arrangement 22. Depending on the blood product or products being propagated, the valve arrangement 22 will direct the blood product or products either to line 26 or to line 28. Thus, the blood products that are to be irradiated will preferably proceed to line 26, to be collected at a later-discussed substantially contiguous, self-contained arrangement, such as a bag, 36, while the blood products that are not to be irradiated will preferably proceed to line 28 and thereby be directed to a bag 30.

The bag 30 may optionally be connected, via a line 32, to the previously mentioned valve arrangement 16. Valve arrangement 16 may, at that point, be selectably switched into a position in which blood products from line 32 are directed, via line 34, back to the patient 10. Thus, valve arrangement 16 could conceivably be embodied by a suitable two-way valve which, in one position, permits the flow of blood from the patient toward cell separator or centrifuge 14 and, in another position, permits the flow of non-irradiated blood products from bag 30 to patient 10.

Although not essential, it may be desirable to completely empty the contents of cell separator or centrifuge 14 at a given time, especially if the cell separator or centrifuge 14 is no longer capable of separating, from the patient's blood, blood products that are to be irradiated. Accordingly, for this purpose, valve arrangement 18 may be configured so as to be switchable from a first position, in which the blood originating from the patient 10 is permitted to proceed to pump 12 and cell separator or centrifuge 14, to a second position, in which blood products that are not to be irradiated and that are being emptied from cell separator or centrifuge 14, pass through pump 12 toward bag 30.

With the blood products to be irradiated having passed through line 26 into a contiguous self-contained arrangement, such as a bag, 36, it may be assumed that, once a predetermined volume of such blood products have accumulated in bag 36, the irradiation process may commence. This process will be described in somewhat more detail further below.

Figure 2:
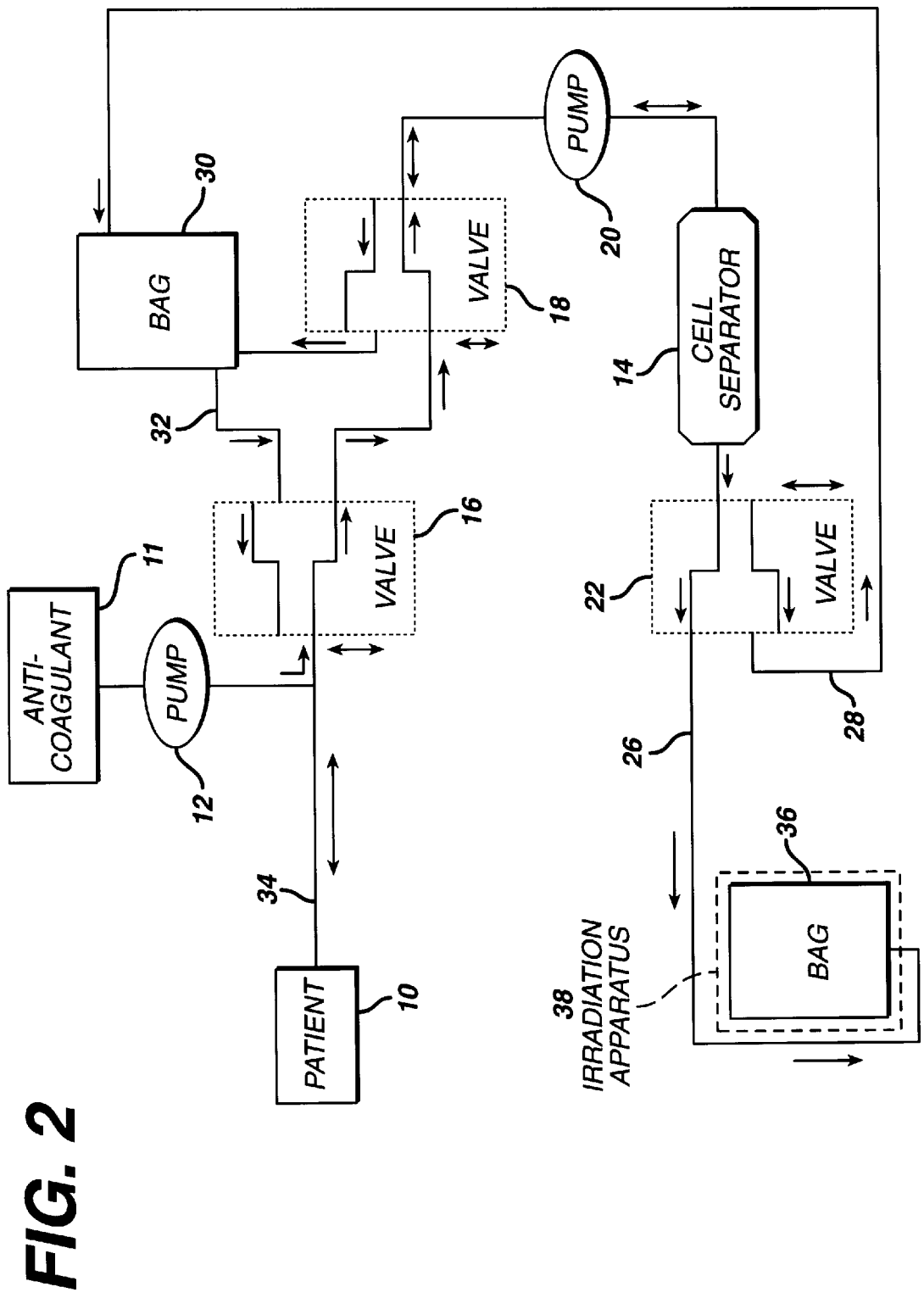
FIG. 2 is substantially the same illustration as FIG. 1, but additionally showing a bag within an irradiation apparatus.

FIG. 1 contemplates some general concepts which themselves may be embodied by any of a number of suitable arrangements. For example, it is conceivable to fill bag 36 with the desired blood products at a location that is remote from the irradiation device. In such an instance, it is conceivable to fill the bag to the desired volume, then close the bag via a suitable closing mechanism, such as a clamp, and then place the bag 36 so clamped into the irradiation apparatus. Alternatively, it is conceivable to position bag 36 within an incorporated or separate irradiation apparatus while it is actually receiving blood products from the call separator or centrifuge 14. Such an arrangement is illustrated schematically in FIG. 2, with the irradiation apparatus being indicated schematically at 38.

Figure 3:
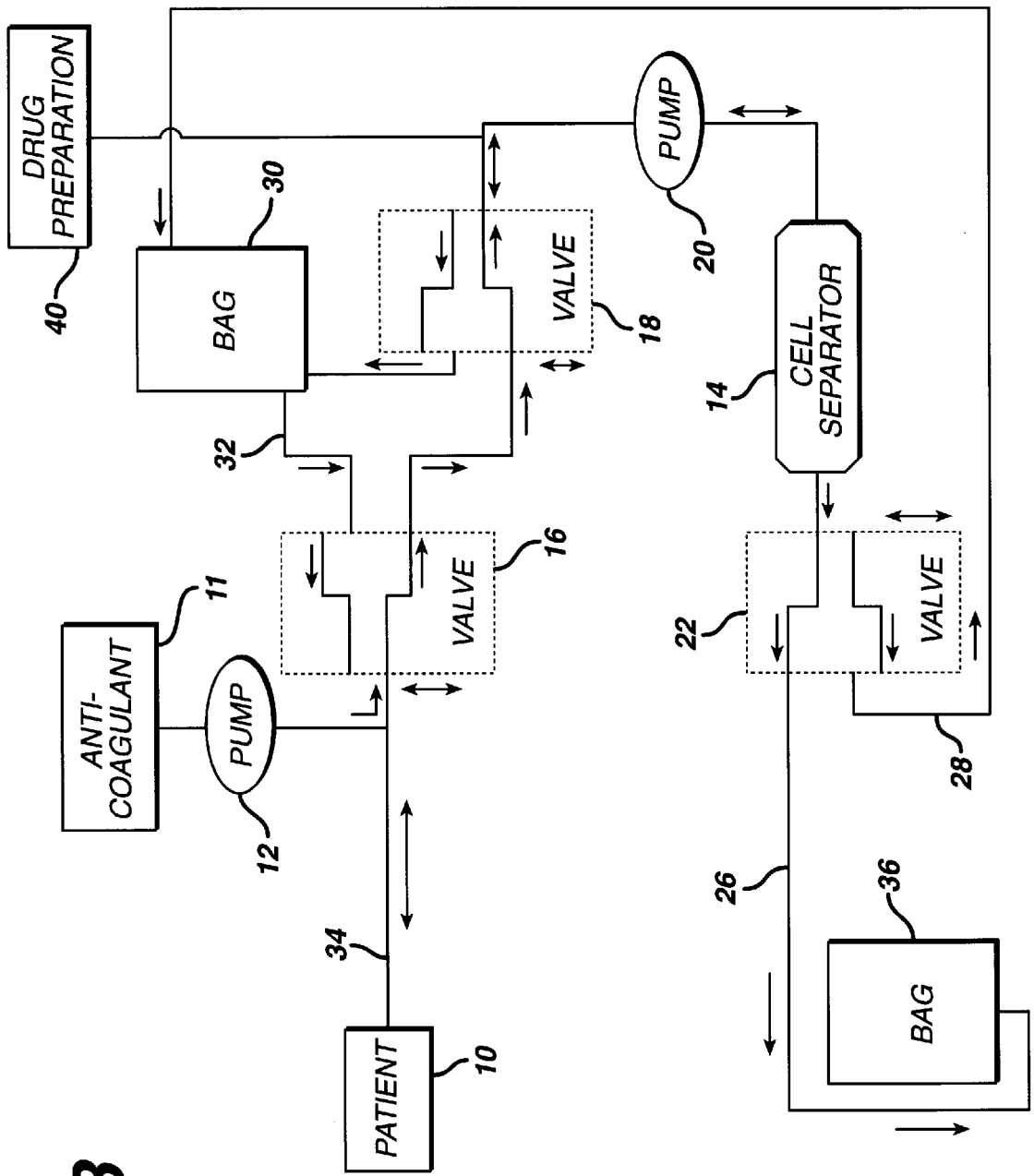
FIG. 3 is substantially the same illustration as FIG. 1, but additionally showing an arrangement for the introduction of a drug preparation.

It is well-known, in the dialysis arts, to introduce, into blood or blood products that are to be irradiated, a drug preparation that is suitable for the purpose of forming photoadducts with DNA in the presence of ultraviolet radiation, in order to adequately treat a patient's blood products in an irradiation process. Such drug preparations are well-known to those of ordinary skill in the art and will thus not be further discussed herein. However, within the scope of the present invention, it is conceivable to introduce such a drug preparation at essentially any suitable stage. For example, the drug preparation could be ingested by the patient internally before withdrawal of his or her blood or, in the alternative, could be introduced extracorporeally. A schematic illustration of a suitable site for the extracorporeal introduction of a drug preparation into a patient's blood is illustrated in FIG. 3, with the source of the drug preparation being indicated at 40.

Figure 4:
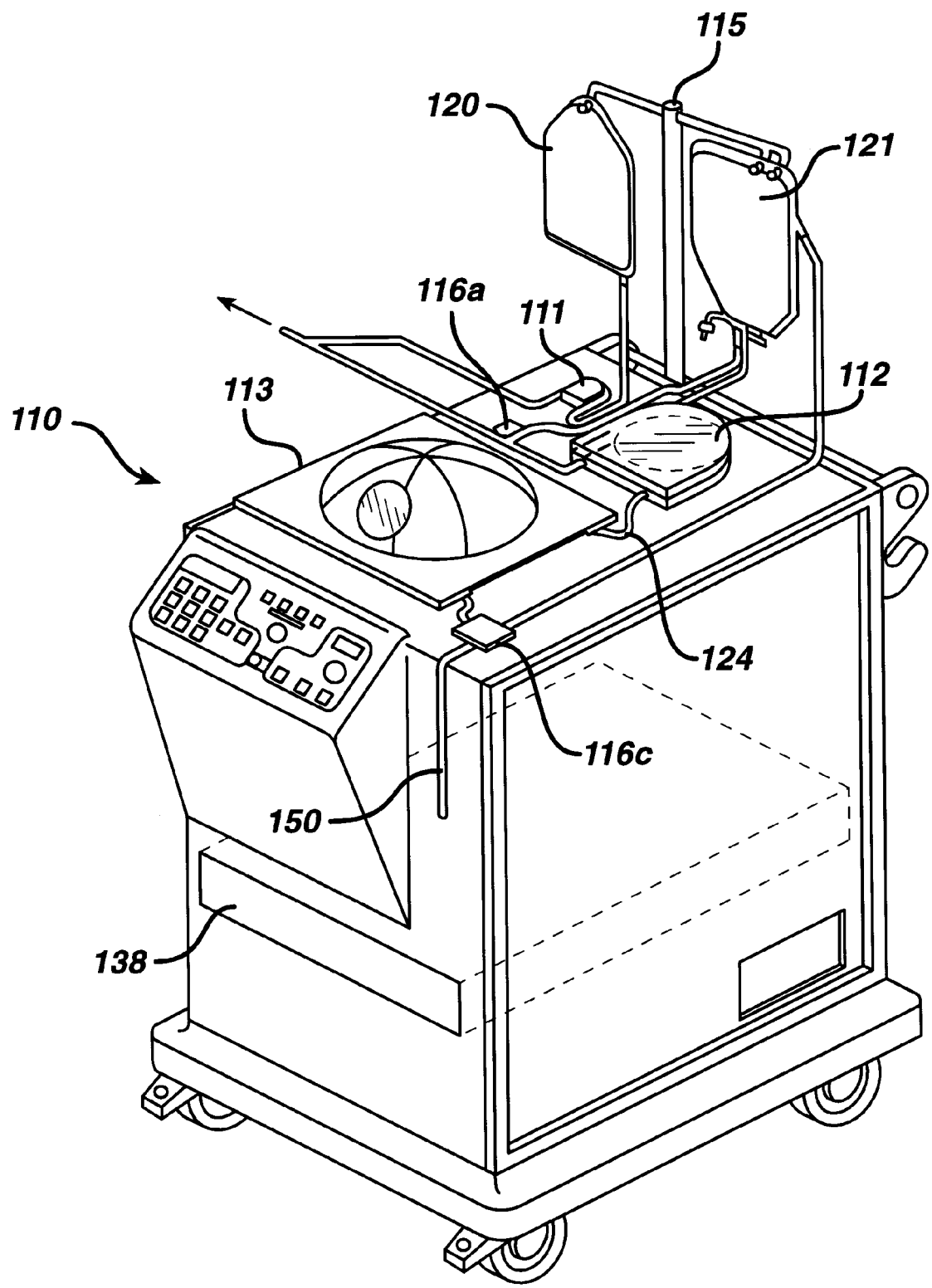
FIG. 4 is an illustration of a possible system into which an irradiation device according to the present invention may be employed.

FIG. 4 illustrates a presently preferred system for the extracorporeal treatment of a patient's blood that may incorporate an irradiation device according to the present invention. However, it is to be understood that the arrangement illustrated in FIG. 4 is provided only as an example and is in no way meant to limit the scope of the present invention.

As shown in FIG. 4, a patient may be connected by venipuncture (or a similar method) well-known in the dialysis arts. The patient's blood, as it flows to the apparatus 110, is preferably infused, under the control of a pump 111, with an anticoagulant agent contained in container or bag 112 hung from stand 115. Control or the flow of patient blood to the remainder of apparatus 110 can largely be controlled by clamping means 116a, which can also have the function of controlling flow in the reverse direction, as well as flow to return container 121 or bag. Clamp 116a can preferably act as an "or" valve.

Preferably, the blood may flow through tubing 124 and through pump 112 into a continuous centrifuge 113.

Other details regarding the apparatus 110 illustrated in FIG. 4 may be found in U.S. Pat. No. 4,692,138 to Troutner, et al. which is hereby incorporated by reference as if set forth in its entirety herein. However, the disclosure now turns briefly to some structural differences of an apparatus 110 according to the present invention, as compared with the apparatus described and illustrated in the aforementioned patent to Troutner, et al.

In accordance with a preferred embodiment of the present invention, as shown in FIG. 4, the line 150 leading away from valve 116c may direct the blood products to be irradiated to a bag (not shown), which bag is preferably already positioned within an irradiation device 138. In a manner to be described further below, a U.V. lamp assembly of irradiation device 138 is preferably oriented substantially horizontally, as opposed to the vertical orientation contemplated by the aforementioned patent to Troutner, et al. Further, in a manner to be described in more detail further below, the aforementioned bag may be closed off in a suitable manner upon a predetermined volume of blood products to be irradiated being present in the bag.

Other details not specifically illustrated in FIG. 4 will be readily appreciated by one of ordinary skill in the art. For example, it is to be understood that irradiation apparatus 138 may preferably be slidably displaceable with respect to tie rest of apparatus 110, in order to facilitate its being pilled out from apparatus 110, conceivably in the manner of a drawer, to permit the placement of a bag in the irradiation apparatus 138. Further, line 150 may preferably be connected to irradiation apparatus 138 in a manner that accounts for the displaceability of irradiation apparatus 138. For example, in one embodiment of the present invention, line 150 could be provided with a sufficient amount of slack in order that it may "follow along" with the displacement of irradiation apparatus 138. Alternatively, a suitable valve mechanism could be provided to permit line 150 to feed into an internal feed line of irradiation apparatus 138 at least when irradation apparatus 138 is disposed fully inside the apparatus 110, which internal feed line itself would lead to the bag disposed within irradiation apparatus 138. Displacement of irradiation apparatus 138 itself could be facilitated, for example, by wheels or other suitable bearings provided on the irradiation apparatus 138 or within apparatus 110.

Of course, as mentioned heretofore, it is also conceivable, within the scope of the present invention, to initially position a bag (e.g., bag 121) remotely from irradiation device 138, with the understanding that the bag would be clamped off and removed to irradiation device 138 upon a predetermined volume of blood products to be irradiated being present in bag.

Figure 5:
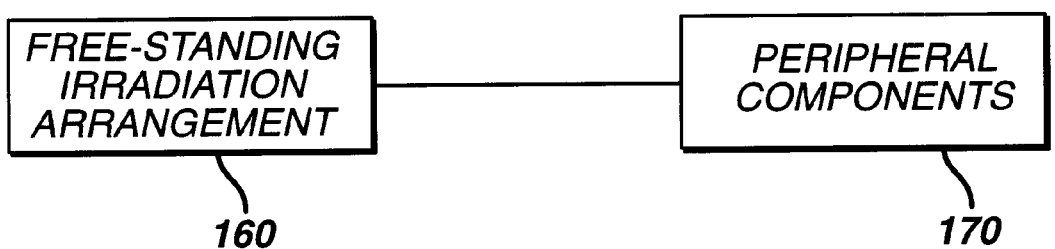
FIG. 5 is a schematic illustration of a free-standing irradiation device.

Although an irradiation arrangement according to the present invention has been described and illustrated with relation to incorporation into an integrated blood product separation and treatment apparatus as described with reference to FIG. 4, the present invention also contemplates that the irradiation equipment be provided as a free-standing arrangement 160, as illustrated schematically in FIG. 5. In this respect, as illustrated in FIG. 5, it is conceivable to provide the majority, if not the totality, of peripheral components described heretofore (i.e., components other than the actual irradiation device itself) at a location remote from that where irradiation is performed. Thus, FIG. 5 illustrates such peripheral components 170. U.S. Pat. Nos. 4,850,995, 4,708,712, and 4,617,279 (to Tie, et al.; Mulzet; and Mulzet, et al., respectively) disclose arrangements for the centrifugal separation of blood that have been found to be particularly suitable for use in conjunction with such a free-standing arrangement.

Figure 6:
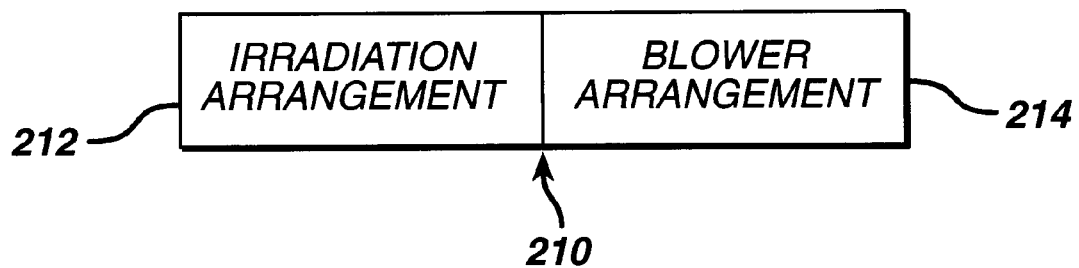
FIG. 6 is a schematic illustration of a general arrangement incorporating an irradiation arrangement and a blower arrangement.

FIG. 6 is a schematic illustration of a general arrangement in accordance with a preferred embodiment of the present invention. Particularly, FIG. 6 schematically illustrates a general irradiation apparatus 210 that includes an irradiation arrangement 212 and a blower arrangement 214. Irradiation arrangement 212 and blower arrangement 214 are interconnected in a manner to be described more fully below. Both may conceivably form the major portion of a free-standing arrangement 160 (as indicated schematically in FIG. 5), with the possible addition of suitable media for supporting irradiation apparatus 212 and blower arrangement 214 (e.g. legs, pods, etc.). The irradiation apparatus 210 could also conceivably be free-standing of its own accord (e.g., supportable on a floor or table without the interposition of supplementary supporting media).

Figure 7:
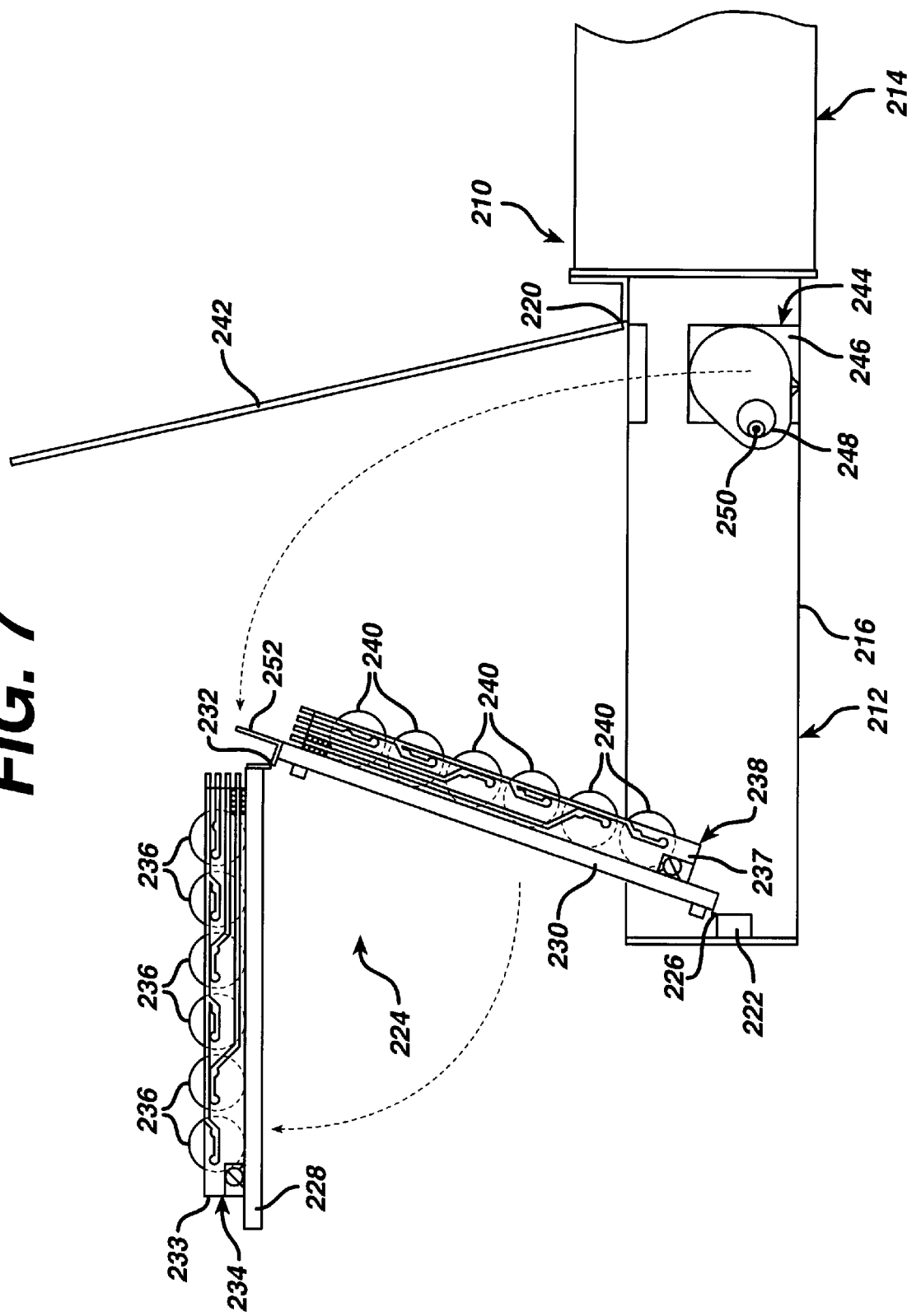
FIG. 7 is a more detailed view of the arrangement illustrated in FIG. 6.

FIG. 7 provides a more detailed view of the irradiation arrangement schematically illustrated in FIG. 6. In accordance with a preferred embodiment of the present invention, irradiation arrangement 212 may preferably be defined primarily by a shroud (or housing) 216 and components disposed therewithin. Preferably, shroud 216 may be selectively opened and closed by way of an upper lid 242 connected by a suitable hinge 220 to the shroud 216.

Prpferably fixedly mounted within shroud 216, to a portion of the shroud frame, is a stop block 222. Preferably, a lamp assembly, in accordance with a preferred embodiment of the present invention, and indicated generally at 224, will be hingedly mounted with respect to block 222 via a suitable hinge arrangement 226.

Within the lamp assembly 224 itself, upper and lower platens (indicated at 228 and 230, respectively) will preferably be hingedly connected with respect to one another via a suitable hinge arrangement 232, whereas the hinge arrangement 226 will preferably connect block 222 with lower platen 230.

In a suitable manner, there will preferably be fixedly mounted at an upper surface of upper platen 228, via support members 233, an upper lamp array 234 that includes a linearly arranged array of individual lamps 236. Likewise, there will preferably be fixedly mounted at a lower surface of lower platen 230, via support members 237, a lower lamp array 238 that includes a linearly arranged array of individual lamps 240.

FIG. 7 illustrates what may be termed an "open" position of cover 242 and also a "fully extended" position of lamp assembly 224. However, it is to be understood that other positions can be achieved in view of the versatility provided by the hinge arrangements 232 and 226.

In this posture, it will be readily appreciated that, for example, with lower platen 230 being oriented in what may be termed a "rest" position, or a lower, generally horizontal position, the upper platen 228 may be hingedly displaced with respect to lower platen 230 in such a manner as to facilitate the placement of an irradiation bag (not shown) on lower platen 230.

It is further to be noted that the multiple hinging action provided by hinges 232 and 226, in any desired combination, can readily facilitate access to the individual lamps 236 and 240, for their inspection, repair or replacement.

Generally indicated at 244 is a motor-and-cam arrangement that may preferably be utilized to displace, in a generally oscillating manner, lamp assembly 224 during an irradiation procedure. As shown in FIG. 7, motor-and-cam arrangement 244 may be embodied by a motor block 246 (containing a suitable motor not otherwise shown), a greater rotating member 248 and a roller 250. Accordingly, with respect to the arrangement illustrated in FIG. 7, there may preferably be provided a flange 252, fixedly connected to and extending from lower platen 230, configured for riding on roller 250 in such a manner that, upon continued rotational displacement of rotatable member 248, flange 252 will pivotally displace (with hinge 222 being the pivot point) in an oscillating manner.

Of course, it is conceivable, within the scope of the present invention, to utilize arrangements other than the cam arrangement 244 illustrated in FIG. 7. For example, it is conceivable to utilize, in the stead of cam arrangement 244, a double-acting piston, a reversible screw-jack, or other suitable means that are controlled in a manner to provide a type of oscillating motion similar to that provided by cam arrangement 244.

Further, it is also to be understood that such oscillating motion may preferably be controlled in a manner deemed most suitable for the purpose of gently agitating the contents of a bag sandwiched between platens 228 and 230 and optimally exposing the same to radiation emitted from lamps 236 and 240.

Also shown in FIG. 7 is a blower arrangement 214, which will be described in more detail herebelow with respect to FIG. 8.

Figure 8:
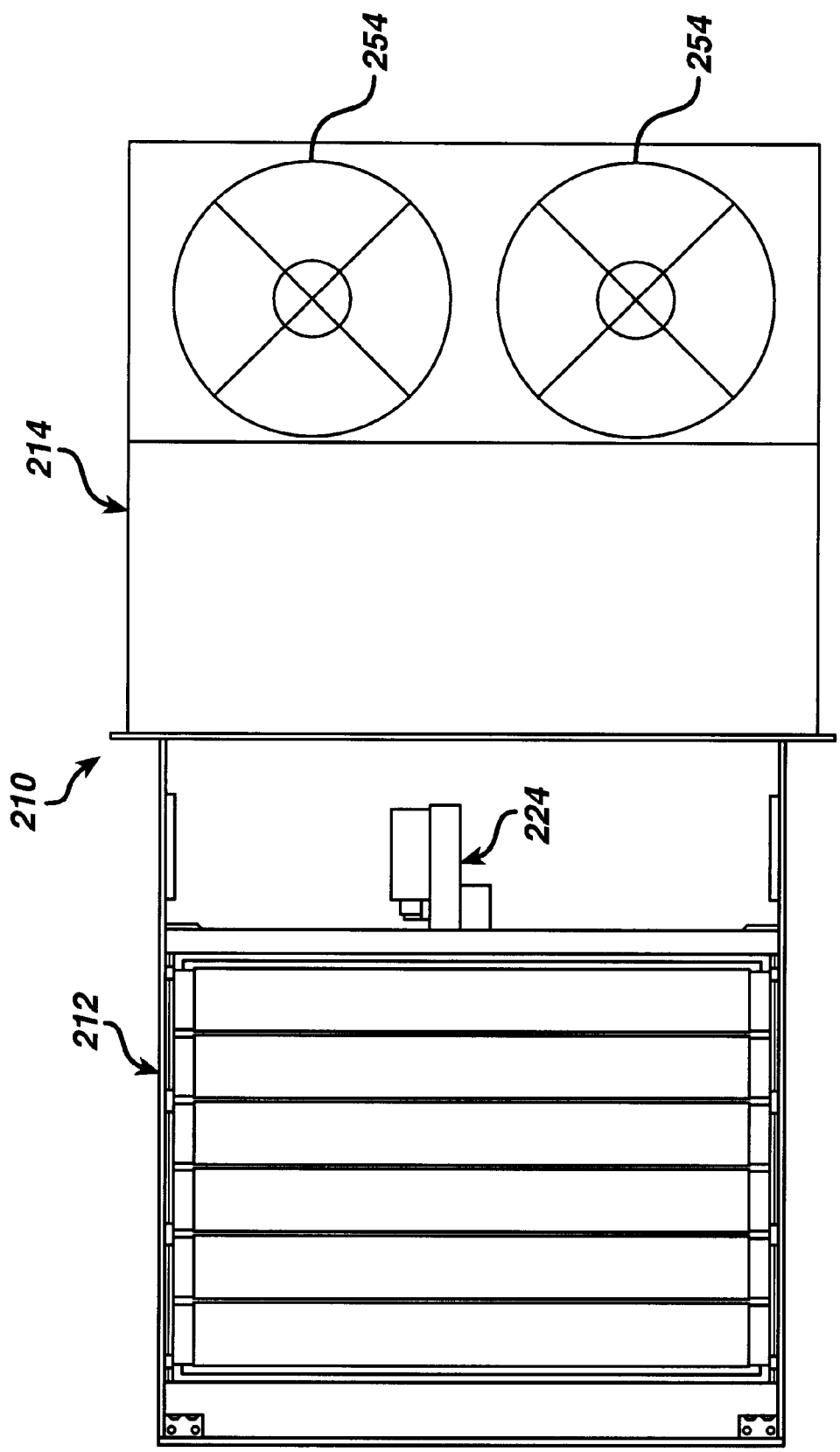
FIG. 8 is a detailed plan view of an irradiation arrangement.
Figure 9:
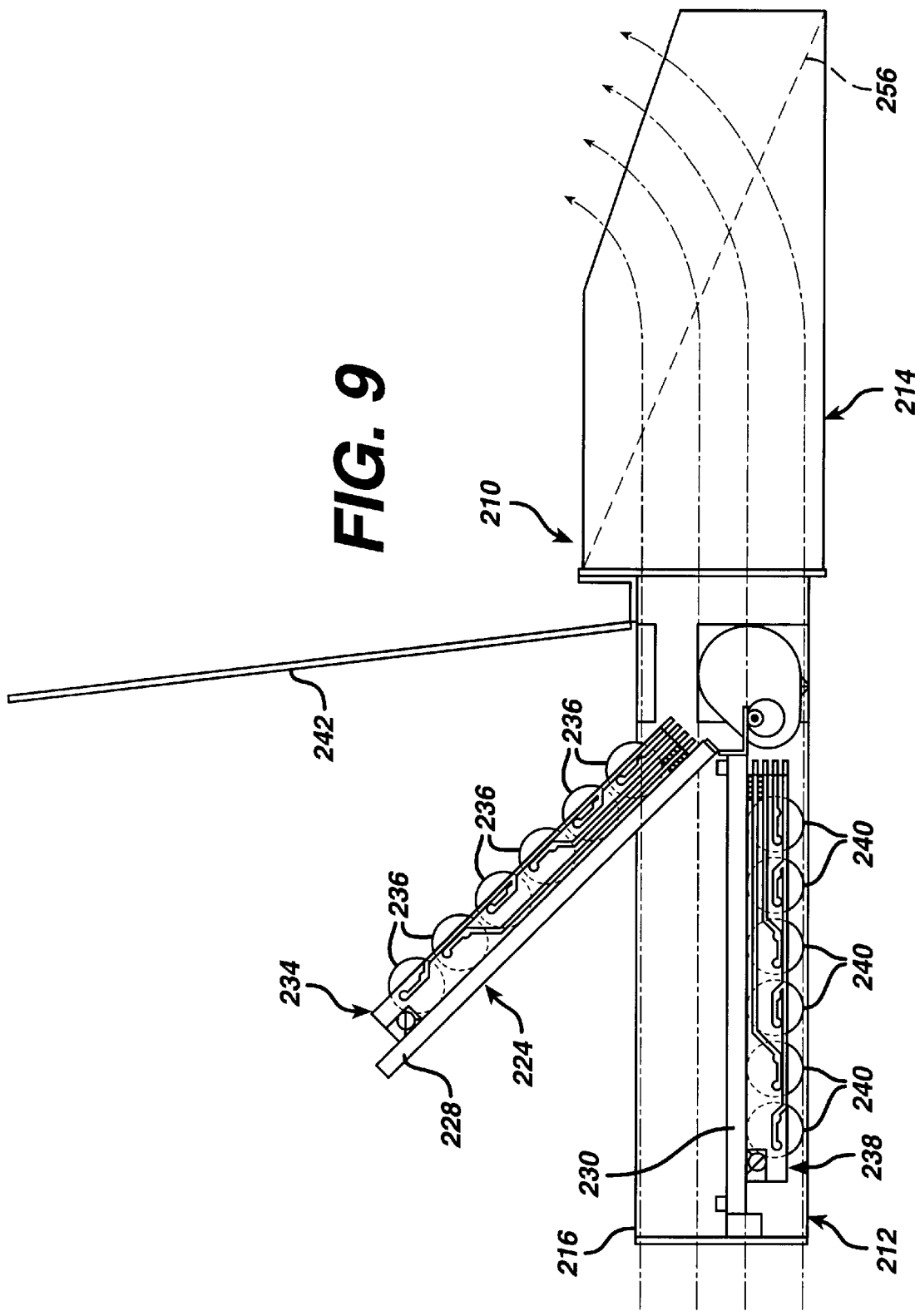
FIGS. 9 and 10 are elevational views of various dispositions of the irradiation arrangement illustrated in FIG. 8.
Figure 10:
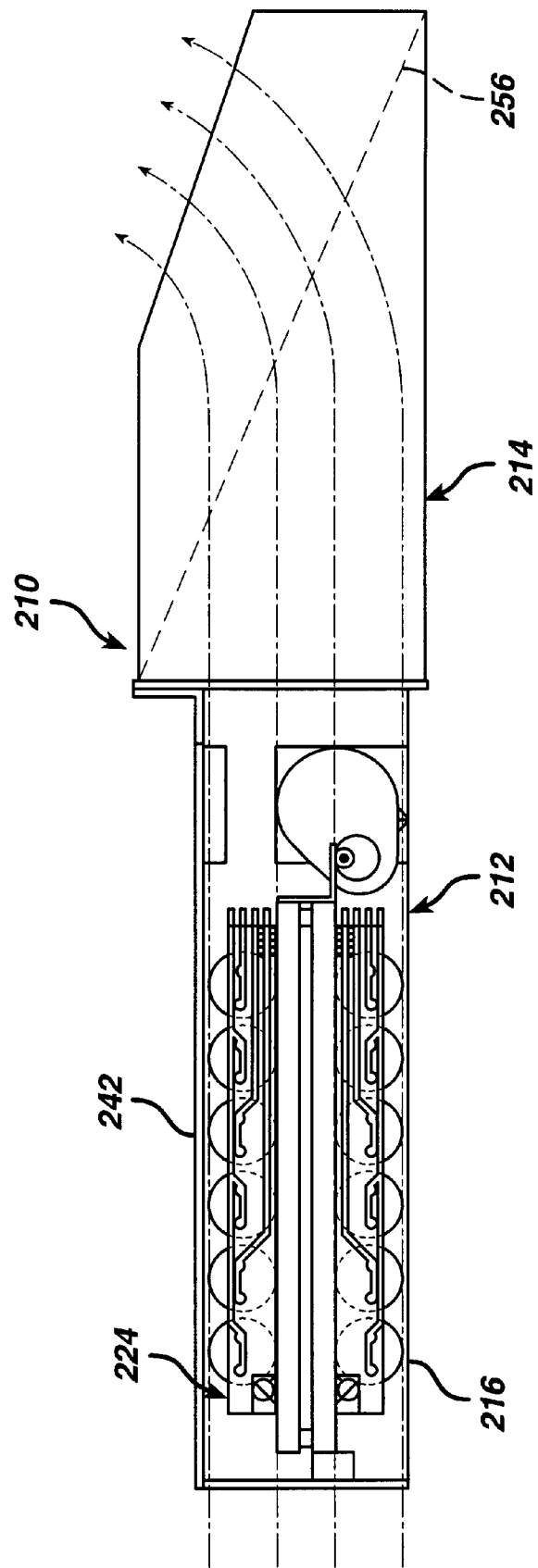

FIG. 8 provides an overhead view of an irradiation arrangement 210 in accordance with a preferred embodiment of the present invention. Particularly, FIG. 8 shows blower arrangement 214 disposed alongside shroud arrangement 212. Further, FIGS. 9 and 10 provide elevational views of an irradiation arrangement according to an embodiment of the present invention. Unless otherwise noted, the disclosure provided herebelow will be relevant to all of FIGS. 8–10.

First, in accordance with at preferred embodiment of the present invention, lamp assembly 224 will preferably be contained within shroud 216 in a manner reminiscent of a "ship-in-a-bottle". Particularly, whereas conventional arrangements have often contemplated static, rigid structures directly incorporating a lamp assembly, the present invention contemplates, in accordance with at least one preferred embodiment, the provision of a lamp assembly 224 as a distinct substructure within a greater housing structure. As has been discussed heretofore, this "substructure" constituted by lamp assembly 224 will preferably be hingedly mounted with respect to shroud 216 in such a manner as to optimally facilitate access to the bulb arrays 234 and 238. However, it may also now be appreciated that shroud 216 can, in accordance with at least one preferred embodiment of the present invention, also effectively serve as a conduit for the propagation therethrough of fresh air, for the purpose of cooling the bulbs 236 and 240. It is believed that, with such an arrangement, bulb cooling, as well as temperature control during irradiation procedures, will be greatly facilitated.

Accordingly, blower arrangement 214 may preferably be configured in such a manner as to provide optimal cooling throughout the interior of shroud 216. For this purpose, blower arrangement 214 will preferably be connected in series with respect to shroud 216 and Will preferably serve to draw air through shroud 216. For this purpose, there may preferably be provided a suitable fan arrangement 254 which, as an example, could include two fans, as shown in FIG. 8. There may also preferably be provided a filter arrangement 256 (illustrated schematically in FIGS. 9 and 10). for the purpose of trapping any aerosols that may have been produced within the system as the result of a leak. Suitable filters would appear to be well-known to those of ordinary skill in the art and will thus not be further described herein. As shown in FIGS. 9 and 10, the filter arrangement 256 may preferably be generally rectilinear in shape and can preferably extend both across substantially the entire width of blower arrangement 214 (see FIG. 8) and from an upper edge at the "inlet" side of blower arrangement 214 to a lower edge at the "outlet" side of blower arrangement 214. Thus, in accordance with a preferred embodiment of the present invention, filter arrangement 256 can extend over a maximal two-dimensional area within blower arrangement 214.

FIG. 10 illustrates irradiation apparatus 210 in a "closed" state; i.e., the lamp assembly 224 is in a completely folded position and lid 242 is closed. In this "closed" state, it is possible to effect an irradiation procedure and simultaneously effect cooling of lamp assembly 224 via blower arrangement 214. FIG. 10 also illustrates, with particular clarity, the manner in which shroud or housing 216 effectively provides a conduit for the through-flow of cooling air for cooling lamp assembly 224 (with parallel arrows indicating the direction of air flow). Lid 242 will preferably be so configured and constructed as to effectively contain U.V. radiation within shroud or housing 216 during an irradiation procedure.

In one embodiment of the present invention, a freestanding irradiation apparatus may be incorporated into a system with a cell separator, and associated pumps and valves, to extract from a patient's blood a quantity of white blood cells with a hematocrit level of probably less than about 2%, treat the white blood cells with a specific drug and U.V. light, then return the treated white blood cells to the patient.

It will be appreciated, from the instant disclosure, that the present invention, in accordance with at least one preferred embodiment, can provide the following advantages, among others:

the functions and capabilities a multi-part recirculating irradiation system essentially being combined into a single bag; and a compact enclosure being provided to optimize air cooling and protect the user from harmful radiation and possible aerosol contamination.

In recapitulation, advantages can be enjoyed by essentially incorporating the functions of a pump chamber, vortex bag, irradiation chamber, and interconnecting tubing into a single simple bag connected by a single tube. It is further contemplated that the functions of a conventional roller pump be replaced by a relatively simple arrangement of rocking glass platens driven by a motor and cam or other suitable oscillation means.

In other words, in accordance with at least one preferred embodiment of the present invention, it is contemplated that a "closed-loop" system of circulating blood products through an irradiation chamber, as described heretofore, be replaced by a much simpler arrangement involving a simple, single bag for being placed inside an irradiation chamber and for being gently displaced so as to evenly expose the blood products contained in the bag to U.V. radiation. In this manner, no circulation via tubing (per se) are necessary in that, preferably, the bag will be closed off at the start of an irradiation process and will only be open again when it is desired that the irradiated blood products be provided to a patient.

Several U.S. patents disclose apparatus and processes, as well as components and concepts associated therewith, that may be utilized in accordance with the embodiments of the present invention. These patents are listed herebelow and are hereby incorporated by reference as if set forth in their entirety herein.

U.S. Pat. No. 4,321,919 to Edelson discloses a general method and system for externally treating human blood.

U.S. Pat. Nos. 4,568,328; 4,578,056 and 4,573,961, to King; King et al.; and King, respectively, disclose automated photophoresis blood portion control methods and apparatus as well as components associated therewith.

U.S. Pat. Nos. 4,643,710, 4,596,547 and 4,681,568 to Troutner disclose valve mechanisms for controlling the flow of fluids in a photoactivation patient treatment system.

U.S. Pat. No. 4,623,328 to Hartranft discloses an arrangement for adding an anti-coagulation reagent to blood or blood products.

U.S. Pat. No. 4,705,498 to Goss discloses a temperature probe for a photoactivation patient treatment system.

U.S. Pat. No. 4,708,715 to Troutner et al. discloses an ultraviolet light array assembly for a photoactivation patient treatment system.

U.S. Pat. No. 4,643,710 to Troutner discloses a valve apparatus for use in a photoactivation patient treatment system.

U.S. Pat. No. 4,573,960 to Goss discloses a three-phase irradiation treatment process.

If not otherwise stated herein, it may be assumed that all components and/or processes described heretofore may, if appropriate, be considered to be interchangeable with similar components and/or processes disclosed elsewhere in the specification, consistent with the spirit and scope of the present invention unless an indication is made to the contrary. That is, it should be appreciated that the apparatus and method of the present invention may be configured and conducted as appropriate for the application. The embodiments described above are to be considered in all respects only as illustrative and not restrictive. The scope of the invention is defined by the following claims rather than by the foregoing description. All changes which come with the meaning and range of equivalency of the claims are to be embraced within their scope.

What is claimed is:

1. An apparatus for treating human blood, said apparatus comprising:

a withdrawing means for withdrawing blood from a human patient;

a separating means for separating blood, connectable to said withdrawing means, into selected blood products;

a storing means, connectable to said separating means, for temporarily storing at least one blood product having been separated by said separating means;

said storing means comprising a contiguous, self-contained arrangement, said contiguous, self-contained arrangement comprising port means for permitting the entry and egress of at least one blood product into and out of said contiguous, self-contained arrangement;

an irradiating means for irradiating at least one blood product held in said contiguous, self-contained arrangement, said irradiating means comprising a radiation source for emitting radiation towards said contiguous, self-contained arrangement;

a supporting means adjacent said irradiating means for supporting said contiguous, self-contained arrangement adjacent said irradiating means while radiation is being emitted towards said contiguous, self-contained arrangement from said radiation source;

an exposure optimizing means for optimizing exposure of at least one blood product being held in said contiguous, self-contained arrangement to radiation emitted by said radiation source while radiation is being emitted towards said contiguous, self-contained arrangement from said radiation source; and said exposure optimizing means for optimizing exposure comprising:

displacing means operable on said contiguous, self-contained arrangement for displacing said contiguous, self-contained arrangement while radiation is being emitted towards said contiguous, self-contained arrangement from said radiation source, to displace the at least one blood product held within said contiguous, self-contained arrangement and maximally expose the at least one blood product to the radiation emitted by said radiation source; and a spacing means associated with said radiation source and said contiguous, self-contained arrangement for maintaining a substantially constant distance between said radiation source and the at least one blood product held in said contiguous, self-contained arrangement during displacement of said contiguous, self-contained arrangement.

2. The apparatus according to claim 1, wherein said displacing means, said contiguous, self-contained arrangement and said radiation source are interconnected whereby said displacing means simultaneously displaces said contiguous, self-contained arrangement and at least a portion of said radiation source while radiation is being emitted towards said contiguous, self-contained arrangement from said radiation source.

3. The apparatus according to claim 2, wherein said displacing means, said supporting means and said radiation source are interconnected whereby said displacing means simultaneously displaces said supporting means and at least a portion of said radiation source while said contiguous, self-contained arrangement is being supported by said supporting means and while radiation is being emitted towards said contiguous, self-contained arrangement from said radiation source.

4. The apparatus according to claim 3, wherein:

said contiguous, self-contained arrangement comprises a bag member being permeable to radiation emitted by said irradiating means; and said radiation source comprises ultraviolet radiation emitting means for emitting ultraviolet radiation towards said bag member with said bag member being supported by said supporting means, to irradiate, with ultraviolet radiation, the at least one blood product held within said bag member.

5. The apparatus according to claim 4, wherein:

a port means of said bag member comprises a closure means for closing said port means at least while ultraviolet radiation is being emitted towards said bag member from said irradiation apparatus, to substantially completely contain the at least one blood product within said bag member and prevent the egress of the at least one blood product out of said bag member while ultraviolet radiation is being emitted towards said bag member from said irradiating means; and said bag member being removable from said supporting means to a location remote from said supporting means subsequent to irradiation of at least one blood product held in said bag member.

6. The apparatus according to claim 5, wherein:

said radiation source comprises a first set of at least one ultraviolet lamp and a second set of at least one ultraviolet lamp, with said supporting means positionable between said first set and said second set;

whereby said supporting means can position said bag member between said first set of at least one ultraviolet lamp and said second set of at least one ultraviolet lamp during irradiation of said at least one blood product; and whereby said displacing means can simultaneously displace said supporting means and said first and second sets of at least one ultraviolet lamp while ultraviolet radiation is being emitted towards said bag member from said irradiating means.

7. The apparatus according to claim 6, wherein said irradiating means comprises:

a hinge between said first set and said second set with respect to one another, whereby to permit hinged displacement of said first set and said second set away from one another and facilitate the positioning of said bag member therebetween.

8. The apparatus according to claim 7, wherein:

said supporting means comprises a lower platen for supporting said bag member and for positioning said bag member between said first set and said second set, said lower platen being fixedly connected to said said second set;

said irradiating means further comprising an upper platen being fixedly connected to said first set of at least one ultraviolet lamp; and wherein said hinge is between said upper and lower platens wherein said upper and lower platens are positionable between a first position, wherein said upper and lower platens are substantially parallel to one another and are in a position to sandwich said bag member, and a second position, wherein said upper and lower platens are hingedly displaced away from one another.

9. The apparatus according to claim 8, further comprising a cooler which comprises:

a housing encasing said first set and said second set;

a fan positioned to draw air through said housing to cool said first set and said second set and exhaust said air through an outlet; and a filter between said outlet and said first set and said second set whereby to filter said air before it is exhausted through said outlet.

10. The apparatus according to claim 9, further comprising:

said lower platen being hingedly connected with respect to said housing; and wherein said housing is shaped and positioned to contain said ultraviolet radiation therewithin during an irradiation process;

said first set of at least one ultraviolet lamp comprising a plurality of ultraviolet lamps;

said second set of at least one ultraviolet lamp comprising a second plurality of ultraviolet lamps;

said housing further comprising a hinged lid, said hinged lid being selectively openable to facilitate extended hinged displacement of said upper platen with respect to said lower platen and of said lower platen with respect to said housing, to thereby facilitate access to said first and second sets; and said displacing means comprising a roller, mounted eccentrically on a rotatable cam member, for imparting a rocking motion to said lower platen.

11. Apparatus for irradiating blood products having been withdrawn from a human patient and having been separated into selected blood products, said apparatus comprising:

a container for temporarily storing at least one blood product, said container comprising a port for permitting the entry and egress of at least one blood product into and out of said container;

a radiation source adjacent said container positioned to emit radiation towards said container;

an agitator being operably connected to said container and said radiation source for simultaneously agitating said container and said radiation source whereby to maintain said container and said radiation source in fixed relationship to one another during said agitation.

12. Apparatus for irradiating blood products having been withdrawn from a human patient and having been separated into selected blood products, said apparatus comprising:

a container for temporarily storing at least one blood product, said container comprising a port for permitting the entry and egress of at least one blood product into and out of said container;

a radiation source positioned to emit radiation towards said container;

a housing encasing said radiation source;

a support adjacent said radiation source supporting said container;

an optimizing means associated with said support and said radiation source for optimizing exposure of at least one blood product being held in said contiguous, self-contained arrangement to radiation emitted by said radiation source while radiation is being emitted towards said contiguous, self-contained arrangement from said radiation source; and a cooling means for cooling said radiation source while radiation is being emitted toward said contiguous, self-contained arrangement from said radiation source.

13. The apparatus according to claim 12, wherein said cooling means comprises a fan positioned to draw air through said housing.

14. The apparatus according to claim 13, wherein:

said radiation source comprises a plurality of ultraviolet lamps; and said housing encases said ultraviolet lamps in such a manner as to provide a conduit for the throughflow of cooling air, provided by said fan, for cooling said ultraviolet lamps, through said housing.

15. The apparatus according to claim 14, wherein said means for optimizing exposure comprises:

an agitator being operably connected to said support and said radiation source to simultaneously agitate said support and said radiation source whereby to hold said support and said radiation source in a fixed relationship to each other during said agitation.

16. The apparatus according to claim 15, incorporated into a system comprising means for withdrawing blood from a human patient which is connected to a means for separating blood, having been withdrawn from a human patient by said withdrawing means, into selected blood products.

17. An apparatus for treating human blood, said apparatus comprising:

a radiation-permeable container for holding at least one human blood product;

a radiation source positioned to irradiate at least one human blood product held in said container; and an agitator being operably connected to said container and said radiation source wherein to simultaneously agitate said container and said radiation source while maintaining a fixed relationship between said container and said radiation source during said agitation.

18. The apparatus according to claim 17, further comprising:

a support supporting the container during irradiation of at least one blood product held within said container;

said agitator being operably connected to said support whereby to simultaneously agitate said radiation source and said support during irradiation of the at least one blood product held in said container.

* * * * *